United States Patent [19]

Keck

[11] Patent Number: 5,430,207

[45] Date of Patent: Jul. 4, 1995

[54] PROCESS FOR DEGRADING COMPLEX HYDROCARBONS TO PRODUCE SIMPLER HYDROCARBONS

[76] Inventor: Jack C. Keck, 5647 Grape, Houston, Tex. 77096

[21] Appl. No.: 185,279

[22] Filed: Jan. 24, 1994

Related U.S. Application Data

[63] Continuation of Ser. No. 64,703, May 20, 1993, abandoned.

[51] Int. Cl.⁶ .............................................. C07C 4/04
[52] U.S. Cl. .................... 585/241; 204/157.6; 204/157.63; 585/648
[58] Field of Search ................. 585/241, 648; 204/157.6, 157.63

[56] References Cited

U.S. PATENT DOCUMENTS

| | | | |
|---|---|---|---|
| 2,838,801 | 6/1958 | DeLong et al. | |
| 4,177,120 | 12/1979 | Zenty | 204/157.52 |
| 4,359,371 | 11/1982 | Bohm et al. | 570/134 |
| 4,408,999 | 10/1983 | Nadkarni et al. | 208/252 |
| 4,413,969 | 11/1983 | McDonald | 425/217 |
| 4,417,948 | 11/1983 | Mayne-Banton et al. | 156/643 |
| 4,419,214 | 12/1983 | Balint et al. | 208/435 |
| 4,432,344 | 2/1984 | Bennington et al. | 126/438 |
| 4,531,950 | 7/1985 | Burt | 55/23 |
| 4,544,789 | 10/1985 | Brown et al. | 585/511 |
| 4,601,864 | 7/1986 | Vreenegoor | 264/37 |
| 4,803,021 | 2/1989 | Werth et al. | 264/25 |
| 4,842,782 | 6/1989 | Portney et al. | 264/1.4 |
| 4,932,747 | 6/1990 | Russell et al. | 350/96.24 |
| 4,971,703 | 11/1990 | Sealock, Jr. et al. | 210/708 |
| 5,015,349 | 5/1991 | Suib et al. | 208/106 |
| 5,084,141 | 1/1992 | Holland | 585/241 |
| 5,181,998 | 1/1993 | Murphy et al. | 208/107 |
| 5,330,623 | 7/1994 | Holland | 585/241 |

OTHER PUBLICATIONS

M. Day and D. M. Wiles, *Photochemical Degradation of Poly(ethylene Terephthalate). I. Irradiation Experiments with the Xenon and Carbon Arc*, Journal of Applied Polymers Science, vol. 16, pp. 175–189 (1972).

R. Srinivasan and Bodel Braren, *Ultraviolet Laser Ablation of Organic Polymers*, Chemical Review, vol. 89, No. 6, pp. 1303–1316 (1989).

S. Lazare and V. Granier, *Ultraviolet Laser Photoablation of Polymers: A Review of Recent Results*, Laser Chem., vol. 10, pp. 25–40, Harwood Academic Publishers GmbH (1989).

*Primary Examiner*—Anthony McFarlane
*Attorney, Agent, or Firm*—Pravel, Hewitt, Kimball & Krieger

[57] ABSTRACT

A process for the recovery of simpler hydrocarbons from complex hydrocarbons such as plastics, oil shale, or tar sands. In the process, the plastic, oil shale, or tar sands are heated in an environment substantially free of oxygen, preferably under partial vacuum, and irradiated with light of a wave length that will excite and break chemical bonds between atoms making up the molecules of plastic, tar sand, or oil shale to produce simpler hydrocarbons useful as fuel.

11 Claims, 2 Drawing Sheets

PROCESS FOR DEGRADING COMPLEX HYDROCARBONS TO PRODUCE SIMPLER HYDROCARBONS

This is a continuation of application Ser. No. 08/064,703, filed on May 20, 1993, now abandoned.

BACKGROUND OF THE INVENTION

1. Field of the Invention

The present invention is of a process for degrading long chain hydrocarbon-containing compositions to produce simpler hydrocarbons suitable for use as a fuel. More specifically, waste plastics (organic polymers) are heated in an oxygen-free atmosphere and subjected to intense light of a wave length that will excite and break chemical bonds causing degradation of the plastic into simpler hydrocarbons suitable for use as fuel. Further, the process may also be applied to tar sands and oil shale to produce simpler hydrocarbons.

2. Description of the Related Art

Recent studies reveal that some of the primary concerns of Americans in the 90's are the continuing pollution of the environment, the availability of sources of environmentally-friendly fuel, and landfill space for disposal of wastes. Ironically, one of the prime constituents of waste is "plastics"—a range of durable organic polymeric components largely made from petroleum-derived hydrocarbons that now pose environmental issues as declining U.S. reserves and political needs dictate a shift to production in environmentally sensitive geographic areas in the United States.

Since plastics are produced from hydrocarbons, the reduction of used or waste plastics back to gaseous hydrocarbons would be desirable thereby reducing the need for hydrocarbon fuels and pressures to exploit reserves in environmentally sensitive areas.

The primary method used to decompose plastic materials, either alone or in combination with other solid waste, is by incineration or oxidation with direct heat. Unfortunately, the burning of plastic materials in their solid state results in the formation of corrosive and toxic products. Decomposition of plastics may also be accomplished by direct pyrolysis. Depending on the materials being processed, this requires temperatures from about 450° C. to 700° C. As such, the considerable amount of energy required with direct pyrolysis makes it cost-prohibitive. In the present invention, the process of breaking the molecular bonds of plastic materials to produce simpler hydrocarbons utilizes pyrolysis in conjunction with radiation without the need for the high energy requirement of conventional pyrolysis and without significant production of corrosive products.

It is well-known that solar ultraviolet radiation causes decomposition of plastic materials. Plastic manufacturers add UV blockers to their products to inhibit this degradation. Earlier studies have suggested the use of sunlight's ultraviolet rays for the purposeful decomposition of plastic materials. M. Day and D. M. Wiles in "Photochemical Degradation of Polyethylene Terephthalate. Irradiation Experiments with the Xenon and Carbon Arc," *Journal of Applied Polymer Science*, vol. 16, pp. 175–89 (1972) suggested the use of 200 to 400 nm wavelength range of sunlight and durations of 1,000 hours of arc lamp exposure. Tests performed with large lamps, however, gave unsatisfactory results. Similarly, Bennington et al. in U.S. Pat. No. 4,432,344 disclosed a method and apparatus for solar destruction of toxic and hazardous materials. The patent described the use of a solar collector to concentrate and focus the sun's energy into a reaction vessel containing a mixture of solids, liquids, or gases to break chemical bonds and then to further oxidize the resulting hazardous and toxic wastes to complete the destruction process.

The excimer laser has been utilized as an ultraviolet wave source for ablative photodecomposition associated with etching or fabricating of polymer materials. Unlike pyrolysis, photo ablation is not a chemical process. Portney et al. in U.S. Pat. No. 4,842,782 disclosed the precision machining of ophthalmic lenses using an excimer laser radiating ultraviolet light. Blum et al. described a technique for the fabrication of devices and circuits composed of multiple layers of materials in U.S. Pat. No. 4,414,059. The Blum process utilized ablative photodecomposition for the selective removal of portions of the resist layer to produce a patterned layer as required in lithography. Photoetching of polyesters, such as polyethylene terephthalate, by ultraviolet radiation was disclosed by Mayne-Banton et al. in U.S. Pat. No. 4,417,948. Both Blum and Mayne-Banton disclosed the use of an ArF excimer laser emitting wavelengths of 193 nm for their etching techniques. The presence of atmospheric oxygen or air was described to enhance the etching process.

More recent studies of the ablation process include a report by R. Srinivasan and Bodel Braren in *Chemical Review*, vol. 89, no. 6, pp. 1303–16 (1989). The article gives an overview of the ablative etching process for numerous polymers. Another comprehensive report titled "Ultraviolet Laser Photo Ablation of Polymers: A Review in Recent Results" was reported by S. Laser and V. Granier of the Photo Physics Laboratory for Molecular Photo Chemistry in Talence, France. This report, published in *Laser Chemistry*, vol. 10, pp. 25–40 (1989) gives a comprehensive review and theoretical analysis of the ablation process.

Recycling of plastics waste through physical methods such as compression and melting was described by McDonald in U.S. Pat. No. 4,413,969. The recovery and reuse of volatile blowing agents used in the production of thermoplastic foams can be found in Burt's U.S. Pat. No. 4,531,950 which discloses a method and apparatus for recovering the gaseous blowing agents which are contained within the cellular structure of foam. In the process, both the blowing agent and the thermoplastic resin are recovered in a form suitable for reuse. Vreenegoor in U.S. Pat. No. 4,601,864 also described a method of drawing off noxious gases during the production of polymeric foam products for recycling purposes.

None of the processes described above, however, suggest the recovery of simple hydrocarbon gases during the pyrolysis of plastics. Nor have they addressed the problems of recovering simple hydrocarbons from oil shale or tar sands.

SUMMARY OF THE INVENTION

The present invention provides a process for reducing long chain hydrocarbon-based polymers and complex molecules containing carbon and hydrogen into shorter molecules suitable for use as fuel. The process includes subjecting the long chain polymers and complex molecules to heat, in a substantially oxygen-free atmosphere, and radiation of a wave length that will excite and break chemical bonds thereby producing molecules of shorter chain length suitable for use a fuel.

In one of its embodiments the invention provides a process for the degradation of "plastics" (long chain organic polymeric compositions including carbon in the chain backbone) into simpler, short chain hydrocarbons suitable for use as fuels. The process includes the steps of heating the plastics to a temperature in the range from about 95° to about 260° C. and subjecting the heated plastic to radiation of a wave length that will excite and break the chemical bonds forming the polymeric chains.

In another embodiment, the invention provides a process for degrading the complex hydrocarbons found in oil shale and tar sands into shorter chain hydrocarbons useful as fuels. In this process, the tar sands or oil shale are heated to a temperature in the range from about 95° to about 260° C., in an atmosphere substantially free of oxygen, and subjected to radiation of a wave length that will excite and break the chemical bonds between atoms making up the complex hydrocarbons to produce short chain simple hydrocarbons suitable for use as fuels.

The invention provides the benefits of solving the problem of waste plastics disposal while at the same time providing an alternative source of fuel. Further, the invention allows the processing of tar sands and oil shale into useful fuels thereby providing an alternative to more traditional crude oil and coal and nuclear fuel sources.

BRIEF DESCRIPTION OF THE DRAWINGS

A better understanding of the present invention can be obtained when the following detailed description of the preferred embodiments is considered in conjunction with the following drawings, in which.

DETAILED DESCRIPTION OF THE PREFERRED EMBODIMENTS

The invention provides a process for the degradation of complex hydrocarbons, including organic polymeric compositions into short chain hydrocarbons suitable for use as fuel. The term "complex hydrocarbons" as used in this specification and claims includes oil shale, tar sands, and the organic polymers that contain carbon and hydrogen, such as polyethylene, polypropylene, polyethylene terephthalate, polystyrene, and the like.

In the process for reducing organic polymeric compositions to simpler hydrocarbons suitable for fuel, it is preferred that the polymer material is of a size that will allow ready heat transfer, mixing and movement through a reactor. Thus, the polymers may be reduced in size by cutting, chopping, or grinding into particles that are preferably less than about 2 inches (50 mm) in diameter.

After size reduction, the polymer particles are heated, preferably in a reactor, in an environment substantially free of oxygen, to a temperature that will cause pyrolysis of the polymeric material when the material is irradiated with a wave length that will excite and break bonds between atoms of the polymeric material thereby producing simpler hydrocarbons useful as fuel. Preferably, the polymers are heated to a temperature approaching its softening point, typically in the range form about 90° C. to about 260 C., at a pressure of about 100 mm Hg to about 400 mm Hg. Heating up to about the softening point allows a faster rate of reaction or bond lysis when radiation is applied.

The heated polymeric compositions are then subjected to radiation, preferably radiation in the wave length 400 to 1 nm, most preferably in the wave length 350 to 5 nm, most preferably ultraviolet radiation in the wave length 310 to 10 nm. Preferably, this light is supplied at an intensity that will break chemical bonds in the polymeric compositions to produce significant quantities of simpler hydrocarbons within a period of time commencing or ranging from about 2 to about 30 seconds, more preferably about 5 to about 10 seconds, most preferably about 5 seconds, depending upon the specific complex hydrocarbon being processed. Further, the amount of radiation needed is dependent upon the energy necessary for breaking the chemical bonds. In a 1,000 lb/hr reactor, radiation of about 150 Watts will be used.

It should be noted that while irradiating heated compositions results in more rapid bond lysis, the composition may be subjected to radiation even during the "heating up" cycle of the process. Thus, simultaneous heating and irradiation takes place.

Figure 1:
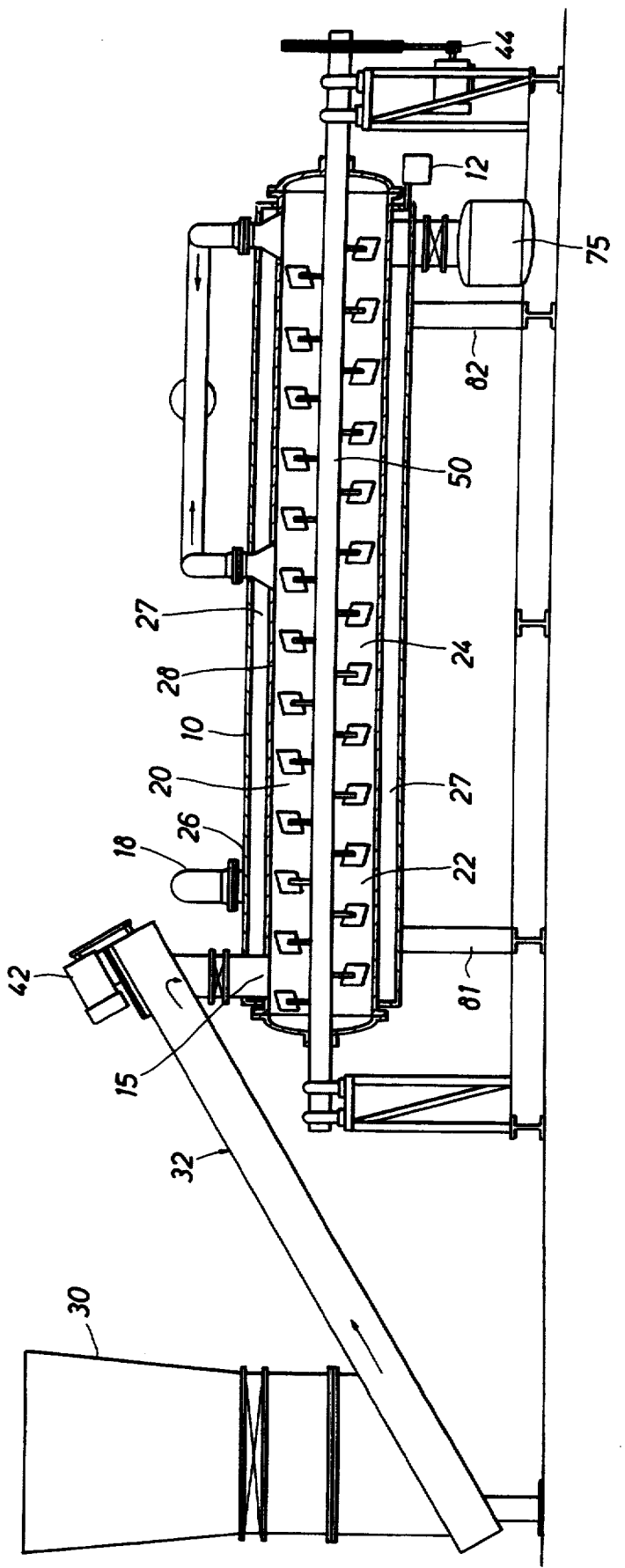
FIG. 1 is a schematic diagram not to scale elevation view of a pilot plant of the process of the invention.
Figure 2:
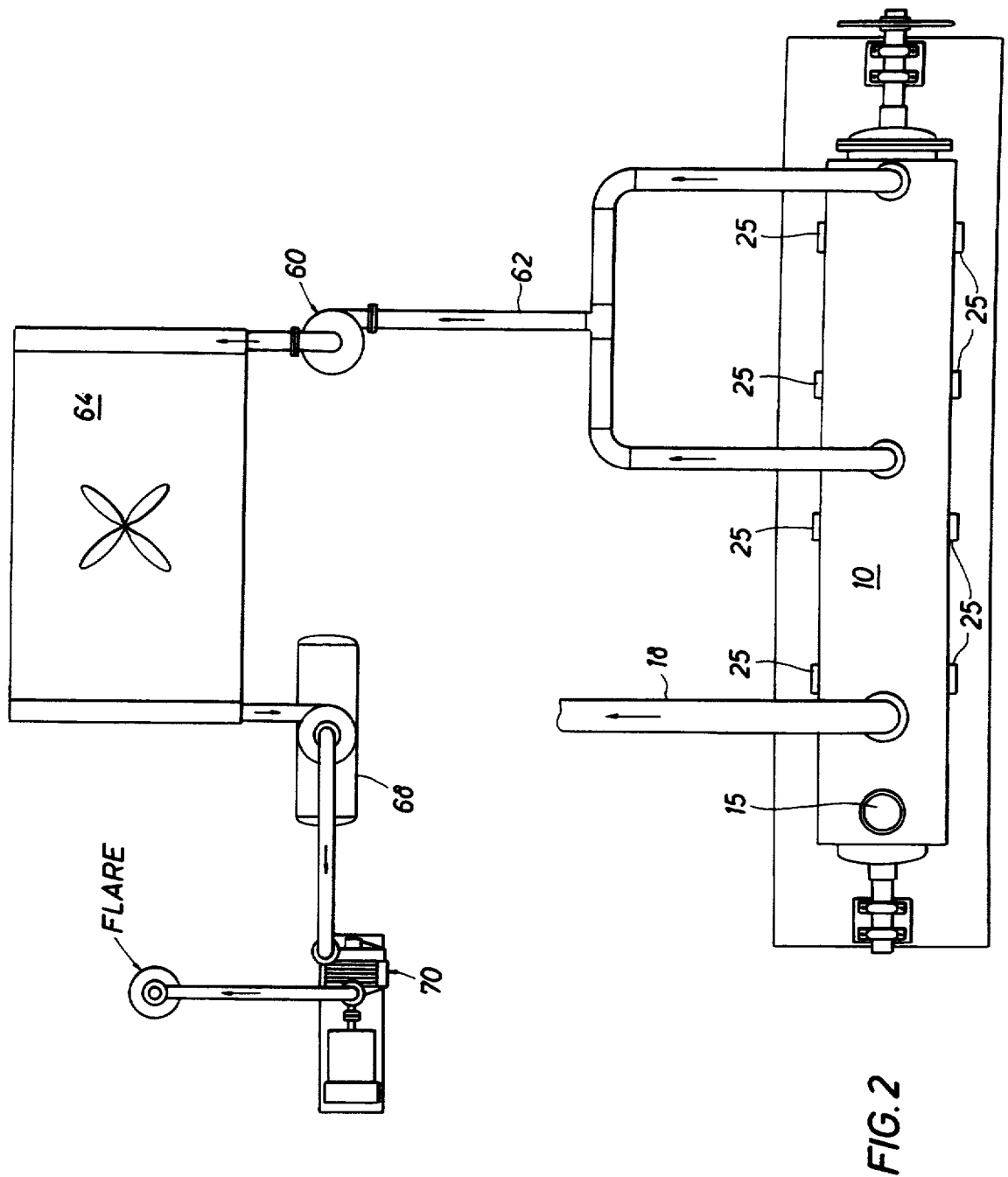
FIG. 2 is a schematic diagram not to scale of a plan view of a plant for practicing the process of the invention.

To facilitate understanding of the invention, it will be described with reference to polymeric compositions and to FIG. 1, it being understood that with modifications, the explanation also applies to oil shale and to tar sands. Polymeric material reduced in size is charged to feed hopper 30 from which it is released at controlled rates onto a continuous feed system, preferably a feed screw conveyor 32 driven by motor 42. The polymeric material enters reactor chamber 20 of reactor vessel 10 through an opening 15 in the top of reactor 10. The reactor chamber 20 is under vacuum drawn by vacuum pump 70 in FIG. 2. The reactor 10, shown in this instance as a horizontal vessel having an inner shell wall 28 and an outer shell wall 26 forming an annular cavity 27, is preferably constructed from stainless steel and is supported, as shown, by legs 81 and 82. A reactor that is, for example, capable of processing about 1,000 lbs/hour (454 kg/hr) of polymeric material, has a working volume of about 192 cubic feet (5.4 m$^3$). This means that the reaction chamber 20 has a diameter of about 2.5 feet (0.8 m), and a length, from seam to seam, of about 20 feet (6.1 m). The reactor chamber 20 is equipped with a paddle conveyor 50, driven by motor 44. At the exemplary rate, it is assumed that shredded plastic feed material has a density of 25 lbs/cubic foot and a residence time within the reactor 10 of approximately 30 to about 60 minutes. Whereas, degradation of heated polymeric material occurs within a few seconds upon exposure to radiation, the material must be preheated to the required temperature. This preheating requires a longer residence time within the reactor.

Polymeric compositions entering the reactor 10 first enter into a heating zone 22 of reactor chamber 20 and are moved along by a paddle conveyor 50. The preferred means for heating the polymeric composition is shown as a shell heater 12 generating hot gases which are blown into annular cavity 27 from which the gases transfer heat to reactor chamber 20 counter currently with flow of polymeric material before being exhausted from the annular cavity 27 through line 18 to vent. The shell heater is capable of heating the polymeric compositions to a temperature in the range from about 95° C. to about 260° C. The desired temperature depends upon the mixture of polymeric compositions being charged and the wave length of radiation that is selected to degrade the polymeric compositions. Typically, the composition is heated to its softening temperature.

The heated polymeric compositions are irradiated with a wave length that will break chemical bonds and reduce the polymeric composition to simpler gaseous hydrocarbons suitable for fuel. While this irradiation may occur in a second, or degradation zone 24 within reactor 10, the heating zone 22 may also be equipped with radiation sources to irradiate heating compositions. Laser charged light in the form of radiation enters degradation zone 24 through a plurality of fused silicon windows 25. These windows should be located to provide maximum irradiation of heated polymeric material and additional windows may be located to allow irradiation of material being heated in heating zone 22.

In the event that the preferred ultraviolet radiation is utilized, then the fused silicon windows 25 should pass preferably approximately 91% of this light. For the 1,000 lb/hour polymer feed rate embodiment, the fused silicon window is approximately 4 inches in diameter and about one-half inch in thickness. Further, the preferred ultraviolet laser is a krypton fluoride excimer laser emitting ultraviolet light at a wave length of about 248 nm and at an energy level consistent with that needed to break chemical bonds of the specific feed, this can vary from about 50 mJ/cm$^2$ to about 450 mJ/cm$^2$. At this level of light intensity, pyrolysis takes place in from about 30 to about 5 seconds. The vaporous hydrocarbons produced are removed through outlet pipe 62 to inlet separator 60 for removing any solid particulates carried over. From inlet separator 60, the hydrocarbon gas is charged to an air cooler 64. During cooling, by-products having higher boiling points may condense. These are removed from the gaseous stream exiting from air cooler 64 in outlet separator 68. The vaporous hydrocarbons may then be used as a source of fuel.

Polymeric char remaining in the degradation zone 24 accumulate in carbon pot 75, which can be periodically emptied.

While the above description relates to the pyrolysis and irradiation of polymeric compositions to produce simpler hydrocarbons, the same apparatus may be used for treating oil shale and tar sands to produce simpler hydrocarbons. Thus, shale or tar sands are comminuted into particulates of a size that would allow radiation to penetrate through the particulate body. These particulates are charged to the feed hopper 30 and fed to the reactor through conveyor 32. In the reactor, the particulates are treated in the same manner as polymeric compositions; namely, they are heated and irradiated while being driven through the reactor by the paddle conveyor. Simple hydrocarbon off gas is removed and residue is collected in the carbon pot 75.

The following examples reflect certain embodiments of the invention and are presented for illustrative purposes only. The invention is not limited to the examples shown.

EXAMPLE 1

Bench Scale Test

A bench scale reactor constructed of stainless steel was used to test the process of this invention. The top of the bench scale reactor had a fused silicon window approximately 4 inches in diameter and one-half inch thick thereby allowing approximately 91% of ultraviolet light to pass through. A large, hinged, covered opening on one side of the reactor allowed access to the center of the chamber. A sample of polyethylene terephthalate cut from soft drink bottles into 2 inch squares, was placed on a platform inside the chamber. The reactor was closed and sealed to maintain integrity. A thermostatically controlled heating coil, situated inside the reactor, was used to heat the sample to approximately 260° C.

The ultraviolet light or radiation was provided by a krypton (KrF) laser, the Lambda Physik model 314, emitting ultraviolet radiation at 248 nm. The heating coil was then activated and the thermostat was set to maintain the desired temperature. The laser controls were set to emit the required energy level and time interval. Upon demand, the laser light was released and entered through the fused silicon window striking the polymer sample for 3 to 5 seconds. The polyethylene terephthalate was vaporized, producing a smokey vapor and leaving a small amount of black char around the edges of the sample.

EXAMPLE 2

Operation of a Continuing Unit as a Pilot Plant

In a proposed test process in this invention, a mixture of chopped plastic scraps is continuously supplied to a reactor where pyrolysis occurred in a catalytic reaction with ultraviolet radiation resulting in ablation that produced combustible gases. Plastic scrap is chopped, using any appropriate shredder, into pieces having an area of not greater than about 6.5 cm$^2$ and dumped into a feed hopper which supplies the chopped plastic to a screw conveyor which in turn conveys the polymer materials into the reactor. The screw conveyor empties the plastic into the top of the reactor so that the scraps drop onto a paddle conveyor system that operates to continuously move the materials through the reactor while lifting and circulating the material. In a heating zone of the reactor, the polymer materials are heated and dried, water vapor being removed by the vacuum system. Heating is provided by a shell heater blowing hot gases into an annular cavity formed by the inner and outer walls of the reactor.

As the polymer materials are moved along through the heating zone to the degradation zone within the reactor, they are heated to a temperature of approximately 260° C. An ultraviolet krypton fluoride laser, Lambda Physik model 315, is used to irradiate the preheated polymer material with ultraviolet light entering the zone through fused silicon windows. The irradiation continues until the plastic scraps are vaporized. The resulting gases or vapors are drawn off by outlet pipes leading to an air cooling system. A cyclone separator removes entrained solids from the hydrocarbon gases before entering the thin-finned air cooler. The gases are cooled by the air cooler and any condensed hydrocarbon liquids are removed in an outlet separator. A vacuum pump is connected to the exhaust line to maintain subatmospheric pressure within the reactor and to recover the hydrocarbon gases which, in the test process, are burned. During pyrolysis, some of the carbon result in char which is removed mechanically from the reactor.

EXAMPLE 3

Commercial Unit

The amount of energy produced by the process of this invention utilizing the heat value of 18,000 BTU per pound of plastic, dry basis, is compared to the amount of energy consumed by the process of this invention.

The electrical consumption required by the process is also determined and compared with the potential electrical output possible when the resulting gases are used as fuel to generate electrical power. The following parameters are given:

| Feed Rate | 10,000 lb./hr. |
|---|---|
| Heating Value | 18,000 BTU/lb. |
| Efficiency Rate | 95% (gasification by weight) |
| Moisture Content | Dry |
| Molecular Weight of Gas | 50 lb./MOL. |

Therefore, in one hour, the heating value of the gas is 171,000,000 BTU. The operation of a commercial system required 6,600,000 BTU/hr for the heaters and 450 kw to process 10,000 pounds of shredded plastics. The resulting 164,400,000 BTU/hr, if used to generate steam for electric power generation, will produce 12,290 kw of electric power.

To determine the heat energy economics of this invention, the heating value measured in BTU of the energy consumed was calculated and compared with the potential energy made available through the process. 164,400,000 BTU/hr. in the form of fuel gases is the net energy available as a result of the process of the invention. This becomes significant in light of the fact that a "Solar Centaur Gas Turbine" requires 41,760,000 BTU/hr. to generate 3,250 kilowatts of electrical power. The net electrical output achieved by recovering hydrocarbons from plastics or other source materials utilizing the process of this invention is approximately 12,290 kw.

Upon reading the above disclosure, a person of ordinary skill in the art will appreciate many variations and modifications of the preferred embodiments as described above. These variations and modifications are within the scope and spirit of the invention as described above and claimed below.

What is claimed is:

1. A process for recovering simpler hydrocarbons from complex hydrocarbons, the process comprising:
   charging complex hydrocarbons to a reactor;
   heating the complex hydrocarbons to a temperature in the range from about 95° to about 260° C. in an environment substantially free of oxygen;
   irradiating the complex hydrocarbons with radiation of a wave length in the range from 1 to 400 nm and an intensity of from about 50 MJ/cm$^2$ to about 450 MJ/cm$^2$ to excite and break chemical bonds between atoms in the complex hydrocarbons to produce simpler hydrocarbons, said irradiating being carried out for a time sufficient to vaporize a substantial proportion of the complex hydrocarbons; and
   recovering simpler hydrocarbons produced.

2. The process of claim 1, wherein the heating and irradiating steps are carried out in a reactor under a pressure of from about 100 to about 400 mm Hg.

3. The process of claim 1, wherein the complex hydrocarbons are organic polymeric compositions.

4. The process of claim 1, wherein the complex hydrocarbons are associated with oil shale.

5. The process of claim 1, wherein the complex hydrocarbons are associated with tar sands.

6. The process of claim 1, wherein the irradiating is irradiating with an excimer laser emitting radiation in the wave length from about 310 to about 10 nm at an energy fluence of at least about 50 mJ/cm$^2$.

7. A process for recovering simpler hydrocarbons from polymeric compositions, the process comprising:
   charging polymeric compositions to a reactor;
   reducing the pressure of the reactor to a pressure in the range from about 100 mm Hg to about 400 mm Hg;
   heating the organic polymeric material to a temperature in the range from about 95° to about 260° C. in an environment substantially free of oxygen;
   irradiating the heated polymeric compositions with radiation in the wave length range from about 310 to about 10 nm and at an intensity of from about 50 to about 450 MJ/cm$^2$ to excite and produce simpler hydrocarbons; and
   recovering simpler hydrocarbons produced.

8. A process for recovering simpler hydrocarbons from complex hydrocarbons, the process comprising:
   charging the complex hydrocarbons to a reactor;
   heating the complex hydrocarbons to a temperature approaching a softening point of the complex hydrocarbons in an environment substantially free of oxygen;
   irradiating the complex hydrocarbons with radiation of a wave length in the range from 1 to 400 nm and at an intensity of from about 50 to about 450 MJ/cm$^2$ to excite and break chemical bonds between atoms in the complex hydrocarbons to produce simpler hydrocarbons, said irradiating being carried out for a time sufficient to vaporize a substantial proportion of the complex hydrocarbons; and
   recovering the simpler hydrocarbons produced.

9. The process of claim 8, wherein the heating is under a vacuum of from 100 to 400 mm Hg.

10. The process of claim 9, wherein the heating is to from about 95° to about 260° C.

11. The process of claim 10, wherein the irradiating is with radiation in the 310 nm to 10 nm wavelength.

* * * * *